Sept. 14, 1954 R. S. MOORE Plant Pat. 1,302

ROSE PLANT

Filed June 8, 1953

WITNESS

Addison E. Avery

INVENTOR

Ralph S. Moore

Webster & Webster

ATTYS.

Patented Sept. 14, 1954

Plant Pat. 1,302

UNITED STATES PATENT OFFICE 1,302

ROSE PLANT

Ralph S. Moore, Visalia, Calif.

Application June 8, 1953, Serial No. 360,400

1 Claim. (Cl. 47—61)

This invention relates to a new and distinct variety of miniature rose plant.

The plant of the present variety is ever-blooming, and is especially characterized by small, dainty buds and semi-double flowers, the buds being a light but variable pink upon opening, and the flowers when full-open being white near the center, shading outwardly to a light pink, with darker pink at the tips. The variety appears to be the freest flowering of all known miniature rose plants.

Another distinctive feature of the present variety of miniature rose plant is its small, light green, almost fern-like foliage; such foliage turning to autumn tints of red, orange, and bronze with the advent of colder fall weather, which the variety very readily withstands. Test plants have successfully wintered over out-of-doors at relatively low temperatures.

An additional feature of the present variety of miniature rose plant is that the plant, which reaches only eight to ten inches in height at maturity, is very compact, being substantially thornless, much branched, and having good vigor for a miniature rose.

A further feature of this variety of miniature rose plant is that the cuttings root very readily at any time of the year, and frequently the cuttings bloom when less than two inches in height.

A still further feature of the present variety of miniature rose plant is its apparent resistance to mildew; tests of many plants under varying growing conditions, and where other varieties were attacked, having failed to establish the existence of mildew on any such test plant.

Being a hardy, vigorous plant for a miniature rose, capable of propagation in a greenhouse or outdoors, such plant is excellent for use either as a pot plant or for garden decoration.

The variety of miniature rose plant herein claimed was originated, as a cross, by me in my experimental nursery at Visalia, county of Tulare, State of California, during the course of an extensive rose plant breeding program seeking miniature roses having distinctive and desirable characteristics for commercial trade. The seed parent was Dancing Doll (unpatented climbing polyantha), and the pollen parent was Oakington Ruby (unpatented miniature). Subsequent to making of the cross, as above, the resultant seeds were planted, and the present variety is one of the seedlings which were produced. Such seedling, when it grew to maturity and bore flowers, was recognized by me as being new and distinctive with respect to the features described herein, and I therefore selected it for reproduction.

After the origination and selection of the variety, as above, I successfully asexually reproduced it by cuttings in my nursery located as aforesaid. These cuttings, of which there were a number, grew to maturity, and were found to carry forward each and every one of such desirable characteristics of the initial plant.

Figure 2:
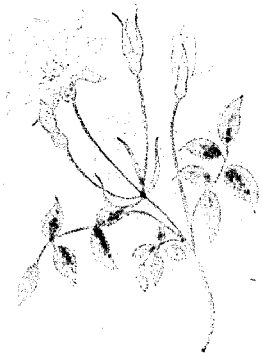
Fig. 2 is a similar view showing a single stem with its flower cluster; one flower being in full bloom, and the remainder in various stages of bud formation.
Figure 1:
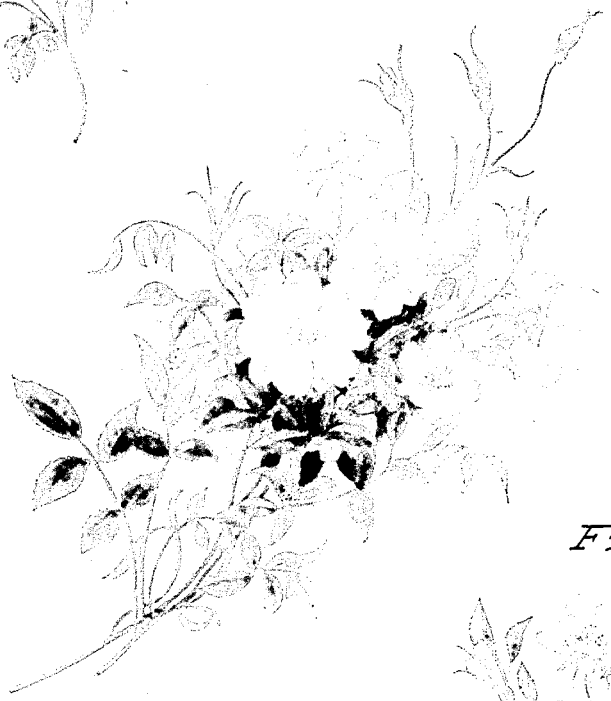
Fig. 1 is a perspective view of a cluster of roses, with stems, leaves, and buds.
Figure 3:
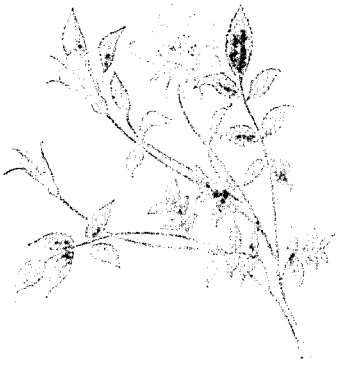
Fig. 3 is a similar view of a single stem, with its flower cluster.

Referring now specifically to the new and distinct variety of rose plant, the following is a detailed description thereof in outline; all major color plate identifications being by Maerz and Paul Dictionary of Color.

Type: Dwarf; bush; greenhouse; outdoor; garden decoration; pot plant.

Class: Miniature.

Flowers:

*Continuity.*—Continuous.

*Fragrance.*—Slight; sweet.

Flowers borne: Singly, several to stem. In irregular cluster. Normal, medium length stems.

Quantity of bloom: Abundant in greenhouse, and outdoors.

Bud:

*Peduncle.*—Medium length; slender; medium erect; light green; almost smooth; few green hairs.

*Before calyx breaks.*—Size—small. Form—pointed; foliaceous appendages on the surface of the bud; slender, foliaceous parts extending beyond the tip of the bud usually equal to ¼ to½ or more of its length. Color.—Light green (20–L–5).

*As calyx breaks.*—Color—varies from light to deep pink.

*As first petal opens.*—Size—small. Form—long; pointed. Color—light to medium pink (50–G–3). Opening—Always opens.

Bloom:

*Size.*—When open—very small, 1 inch to 1⅛ inches.

*Petalage.*—Semi-double; from 15 to 20 petals; arranged regularly.

*Form.*—Flat, open at first, becoming very flat and open. Petals rolled outward at maturity.

Petals: Soft. Satiny both inside and outside.

*Shape.*—Outside—obovate. Intermediate—obovate, lanceolate. Inside—lanceolate.

*Color.*—On newly opened flowers—white at base, shading outward to a light pink (50–J–4), shading to darker pink at tips (50–D–9). On flowers open several days—pink color lightens, shading to 50–K–6 at tips.

*Flower longevity.*—Bush in garden—three to five days in October. Cut roses grown outdoors, kept at living room temperatures—three to four days in October. Cut roses grown in greenhouse, kept at living room temperatures—three to four days in April.

Reproductive organs:

*Stamens.*—Medium number. Arranged regularly about pistils.

*Filaments.*—Short; with anthers. Color—white.

*Anthers.*—Small. All open at once. Color—yellow.

*Pollen.*—Sparse. Color—yellow.

*Pistils.*—Medium number.

*Styles.*—Short; bunched.

*Stigma.*—Red.

*Ovaries.*—All enclosed in calyx.

*Hips.*—Globular; reddish; smooth; thin walls; very few.

*Sepals.*—Permanent; long; spear shaped. Drop before seed ripens.

*Seeds.*—Very few; small.

Foliage:

*Leaves.*—Compound of five to seven; abundant; very small; thin; glossy.

*Leaflets.*—Oval, with apex acute. Base round. Margin serrate.

*Color.*—Mature leaves—light green (22–L–7). Young leaves—somewhat lighter green (20–L–5).

*Rachis.*—Light. Smooth grooved on upper side. Sparsely thorny on under side.

*Stipules.*—Short. Narrow, with moderately long points turning out at an angle of about 45°.

*Disease.*—Apparently resistant to mildew.

Growth:

*Habit.*—Dwarf; bushy; much branched.

*Growth.*—Good vigor for a miniature rose.

*Canes.*—Light.

*Main stems.*—Green (20–L–5). Thorns—none. Prickles—none. Hairs—none.

*Branches.*—Green. Thorns—none. Prickles—none. Hairs—none.

*New shoots.*—Green. Thorns—none. Prickles—none. Hairs—none.

The miniature rose plant and its flowers as herein described may vary in slight detail due to climatic and soil conditions under which the varety may be grown.

Having thus described my invention I claim:

A new and distinct variety of miniature rose plant characterized by small, dainty buds and semi-double flowers, the buds upon opening being a light variable pink and the fully open flowers being white near the center, shading outward to a light pink, and then shading to a darker pink at the tips; further characterized by a plant which is very short and compact, substantially thornless, ever-blooming, very free flowering, and having small light green, almost fern-like foliage apparently resistant to mildew and which turns to autumn tints of red, orange, and bronze when subject to cold fall weather; and additionally characterized by ease of reproduction from cuttings.

No references cited.